United States Patent
Finke et al.

(10) Patent No.: US 8,086,458 B2
(45) Date of Patent: Dec. 27, 2011

(54) AUDIO SIGNAL DE-IDENTIFICATION

(75) Inventors: Michael Finke, Pittsburgh, PA (US); Detlef Koll, Pittsburgh, PA (US)

(73) Assignee: Multimodal Technologies, LLC, Pittsburgh, PA (US)

( * ) Notice: Subject to any disclaimer, the term of this patent is extended or adjusted under 35 U.S.C. 154(b) by 175 days.

(21) Appl. No.: 12/258,103

(22) Filed: Oct. 24, 2008

(65) Prior Publication Data

US 2009/0048834 A1    Feb. 19, 2009

Related U.S. Application Data

(63) Continuation of application No. 11/064,343, filed on Feb. 23, 2005, now Pat. No. 7,502,741.

(51) Int. Cl.
G06Q 50/00 (2006.01)
G10L 15/26 (2006.01)
G06F 17/21 (2006.01)

(52) U.S. Cl. ............. 704/270; 704/273; 705/2; 705/3

(58) Field of Classification Search .......... 704/231, 704/251, 270, 273; 705/1, 2, 3
See application file for complete search history.

(56) References Cited

U.S. PATENT DOCUMENTS

| | | | |
|---|---|---|---|
| 6,829,582 B1 * | 12/2004 | Barsness | 704/275 |
| 6,963,837 B1 * | 11/2005 | Finke et al. | 704/256 |
| 7,136,684 B2 * | 11/2006 | Matsuura et al. | 455/575.2 |
| 7,257,531 B2 * | 8/2007 | Holub | 704/235 |
| 7,502,741 B2 * | 3/2009 | Finke et al. | 704/270 |
| 7,523,316 B2 * | 4/2009 | Cheng et al. | 713/182 |
| 7,584,103 B2 * | 9/2009 | Fritsch et al. | 704/257 |
| 7,640,158 B2 * | 12/2009 | Detlef et al. | 704/235 |
| 7,716,040 B2 * | 5/2010 | Koll et al. | 704/9 |
| 7,844,464 B2 * | 11/2010 | Schubert et al. | 704/270.1 |
| 7,869,996 B2 * | 1/2011 | Carraux et al. | 704/235 |
| 7,933,777 B2 * | 4/2011 | Koll | 704/270.1 |
| 2004/0199782 A1 * | 10/2004 | Arnold | 713/200 |
| 2005/0165623 A1 * | 7/2005 | Landi et al. | 705/2 |
| 2006/0089857 A1 * | 4/2006 | Zimmerman et al. | 705/2 |
| 2009/0132239 A1 * | 5/2009 | Finke et al. | 704/200.1 |

* cited by examiner

Primary Examiner — Martin Lerner
(74) Attorney, Agent, or Firm — Robert Plotkin, P.C.

(57) ABSTRACT

Techniques are disclosed for automatically de-identifying spoken audio signals. In particular, techniques are disclosed for automatically removing personally identifying information from spoken audio signals and replacing such information with non-personally identifying information. De-identification of a spoken audio signal may be performed by automatically generating a report based on the spoken audio signal. The report may include concept content (e.g., text) corresponding to one or more concepts represented by the spoken audio signal. The report may also include timestamps indicating temporal positions of speech in the spoken audio signal that corresponds to the concept content. Concept content that represents personally identifying information is identified. Audio corresponding to the personally identifying concept content is removed from the spoken audio signal. The removed audio may be replaced with non-personally identifying audio.

22 Claims, 7 Drawing Sheets

AUDIO SIGNAL DE-IDENTIFICATION

CROSS REFERENCE TO RELATED APPLICATIONS

This application is a continuation of commonly-owned Ser. No. 11/064,343, filed Feb. 23, 2005, now U.S. Pat. No. 7,502,741, issued on Mar. 10, 2009, entitled, "Audio Signal De-Identification."

This application is related to the following commonly-owned U.S. patent applications, both of which are hereby incorporated by reference:

Ser. No. 10/923,517, filed on Aug. 20, 2004, entitled "Automated Extraction of Semantic Content and Generation of a Structured Document from Speech"; and Ser. No. 10/922, 513, filed on Aug. 20, 2004, entitled "Document Transcription System Training."

BACKGROUND

1. Field of the Invention

The present invention relates to techniques for performing automated speech recognition and, more particularly, to techniques for removing personally identifying information from data used in human-assisted transcription services.

2. Related Art

It is desirable in many contexts to generate a written document based on human speech. In the legal profession, for example, transcriptionists transcribe testimony given in court proceedings and in depositions to produce a written transcript of the testimony. Similarly, in the medical profession, transcripts are produced of diagnoses, prognoses, prescriptions, and other information dictated by doctors and other medical professionals.

At first, transcription was performed solely by human transcriptionists who would listen to speech, either in real-time (i.e., in person by "taking dictation") or by listening to a recording. One benefit of human transcriptionists is that they may have domain-specific knowledge, such as knowledge of medicine and medical terminology, which enables them to interpret ambiguities in speech and thereby to improve transcript accuracy.

It is common for hospitals and other healthcare institutions to outsource the task of transcribing medical reports to a Medical Transcription Service Organization (MTSO). For example, referring to FIG. 1, a diagram is shown of the typical dataflow in a conventional medical transcription system 100 using an outsourced MTSO. A physician 102 dictates notes 104 into a dictation device 106, such as a digital voice recorder, personal digital assistant (PDA), or a personal computer running dictation software. The dictation device 106 stores the spoken notes 104 in a digital audio file 108.

Figure 1:
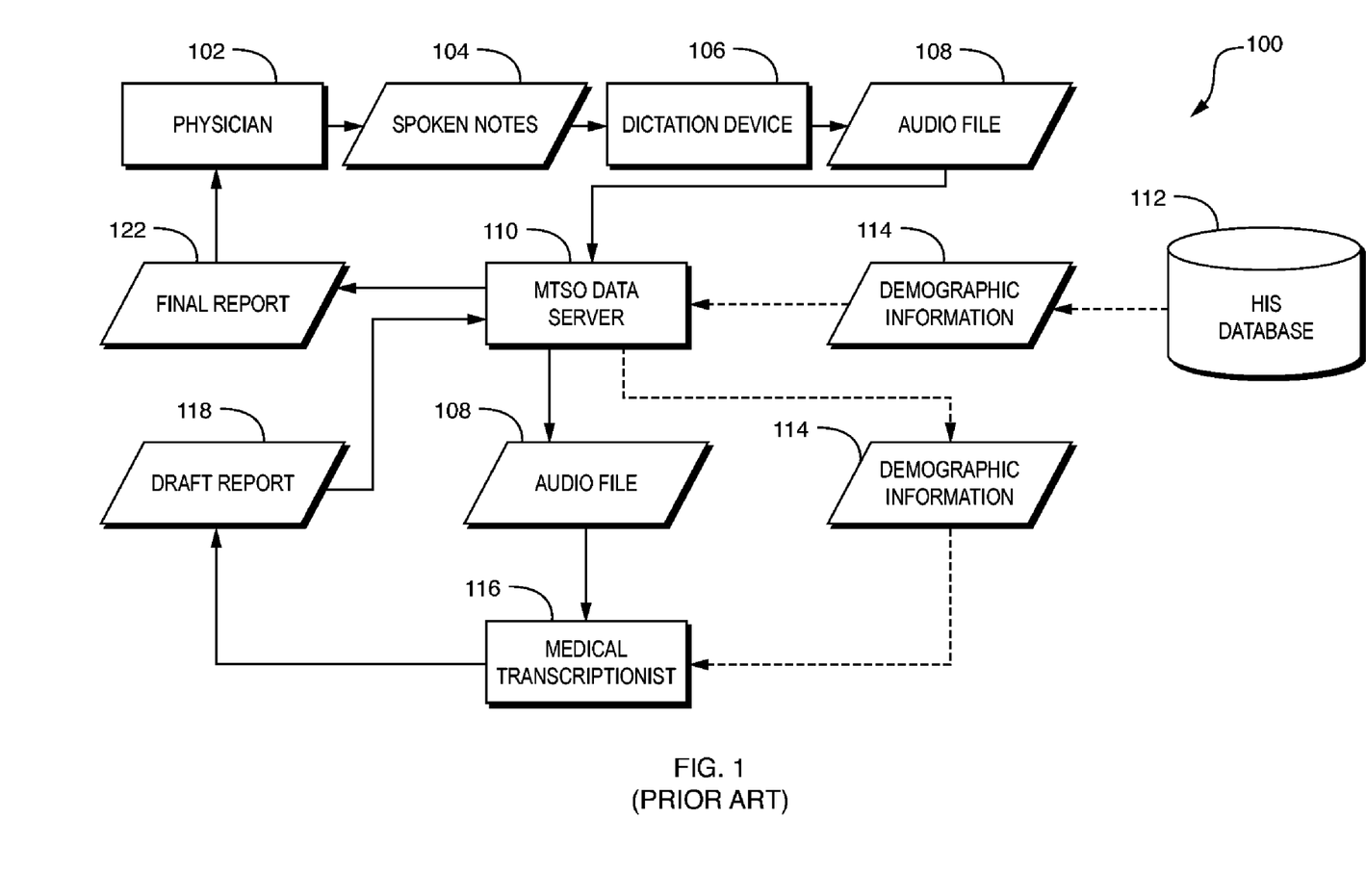
FIG. 1 is a diagram of the typical dataflow in a conventional medical transcription system using an outsourced Medical Transcription Service Organization (MTSO)

The audio file 108 is transmitted to a data server 110 at the MTSO. Note that if the dictation device 106 is a telephone, the audio file 108 need not be stored at the site of the physician 102. Rather, the telephone may transmit signals representing the notes 104 to the data server 110, which may generate and store the audio file 108 at the site of the MTSO data server 110.

The MTSO may interface to a hospital information system (HIS) database 112 which includes demographic information regarding, for example, the dictating physician 102 (such as his or her name, address, and specialty), the patient (such as his or her name, date of birth, and medical record number), and the encounter (such as a work type and name and address of a referring physician). Optionally, the MTSO data server 110 may match the audio file 108 with corresponding demographic information 114 from the HIS database 112 and transmit the audio file 108 and matched demographic information 114 to a medical transcriptionist (MT) 116. Various techniques are well-known for matching the audio file 108 with the demographic information 114. The dictation device 106 may, for example, store meta-data (such as the name of the physician 102 and/or patient) which may be used as a key into the database 112 to identify the corresponding demographic information 114.

The medical transcriptionist 116 may transcribe the audio file 108 (using the demographic information 114, if it is available, as an aid). The medical transcriptionist 116 transmits the report 118 back to the MTSO data server 110. Although not shown in FIG. 1, the draft report 118 may be verified and corrected by a second medical transcriptionist to produce a second draft report. The MTSO (through the data server 110 or some other means) transmits a final report 122 back to the physician 102, who may further edit the report 122.

Sensitive information about the patient (such as his or her name, history, and name/address of physician) may be contained within the notes 104, the audio file 108, the demographic information 114, the draft report 118, and the final report 122. As a result, increasingly stringent regulations have been developed to govern the handling of patient information in the context illustrated by FIG. 1. Even so, sensitive patient information may travel through many hands during the transcription process. For example, the audio file 108 and admission-discharge-transmission (ADT) information may be transferred from the physician 102 or HIS database 112 to the off-site MTSO data server 110. Although the primary MTSO data server 110 may be located within the U.S., an increasing percentage of data is forwarded from the primary data server 110 to a secondary data server (not shown) in another country such as India, Pakistan, or Indonesia, where non-U.S. persons may have access to sensitive patient information. Even if data are stored by the MTSO solely within the U.S., non-U.S. personnel of the MTSO may have remote access to the data. Furthermore, the audio file 108 may be distributed to several medical transcriptionists before the final report 122 is transmitted back to the physician 102. All sensitive patient information may be freely accessible to all handlers during the transcription process.

What is needed, therefore, are improved techniques for maintaining the privacy of patient information during the medical transcription process.

SUMMARY

Techniques are disclosed for automatically de-identifying audio signals. In particular, techniques are disclosed for automatically removing personally identifying information from spoken audio signals and replacing such information with non-personally identifying information. De-identification of an audio signal may be performed by automatically generating a report based on the spoken audio signal. The report may include concept content (e.g., text) corresponding to one or more concepts represented by the audio signal. The report may also include timestamps indicating temporal positions of speech in the audio signal that corresponds to the concept content. Concept content that represents personally identifying information is identified. Portions of the audio signal that correspond to the personally identifying concept content are removed from the audio signal. The removed portions may be replaced with non-personally identifying audio signals.

For example, in one aspect of the present invention, techniques are provided for: (A) identifying a first portion of an original audio signal, the first portion representing sensitive information, such as personally identifying information; and (B) producing a modified audio signal in which the identified first portion is protected against unauthorized disclosure.

The identified first portion may be protected in any of a variety of ways, such as by removing the identified first portion from the original audio signal to produce the modified audio signal, whereby the modified audio signal does not include the identified first portion. Alternatively, for example, a security measure may be applied to the identified first portion to produce the modified audio signal, wherein the identified first portion in the modified audio signal is protected against unauthorized disclosure. The security measure may, for example, include encrypting the identified first portion.

The first portion may be identified in any of a variety of ways, such as by identifying a candidate portion of the original audio signal, determining whether the candidate portion represents personally identifying information, and identifying the candidate portion as the first portion if the candidate portion represents personally identifying information.

Furthermore, the first audio signal portion may be replaced with a second audio signal portion that does not include personally identifying information. The second audio signal may, for example, be a non-speech audio signal or an audio signal representing a type of concept represented by the identified portion.

The first portion may, for example, be identified by: (1) generating a report, the report comprising: (a) content representing information in the original audio signal, and (b) at least one timestamp indicating at least one temporal position of at least one portion of the original audio signal corresponding to the content; (2) identifying a first personally identifying concept in the report; (3) identifying a first timestamp in the report corresponding to the first personally identifying concept; and (4) identifying a portion of the original audio signal corresponding to the first personally identifying concept by using the first timestamp. The first personally identifying concept may be removed from the report to produce a de-identified report.

The de-identified audio signal may be transcribed to produce a transcript of the de-identified audio signal. The transcript may, for example, be a literal or non-literal transcript of the de-identified audio signal. The transcript may, for example, be produced using an automated speech recognizer.

Other features and advantages of various aspects and embodiments of the present invention will become apparent from the following description and from the claims.

DETAILED DESCRIPTION

The term "personally identifying information" refers herein to any information that identifies a particular individual, such as a medical patient. For example, a person's name is an example of personally identifying information. The Health Insurance Portability and Accountability Act of 1996 (HIPAA) includes a variety of regulations establishing privacy and security standards for personally identifying health care information. For example, HIPAA requires that certain personally identifying information (such as names and birthdates) be removed from text reports in certain situations. This process is one example of "de-identification." More generally, the term "de-identification" refers to the process of removing, generalizing, or replacing personally identifying information so that the relevant data records are no longer personally identifying. Typically, however, personally identifying information is not removed from audio recordings because it would be prohibitively costly to do so using conventional techniques.

In embodiments of the present invention, techniques are provided for performing de-identification of audio recordings and other audio signals. In particular, techniques are disclosed for removing certain pre-determined data elements from audio signals.

Figure 2A:
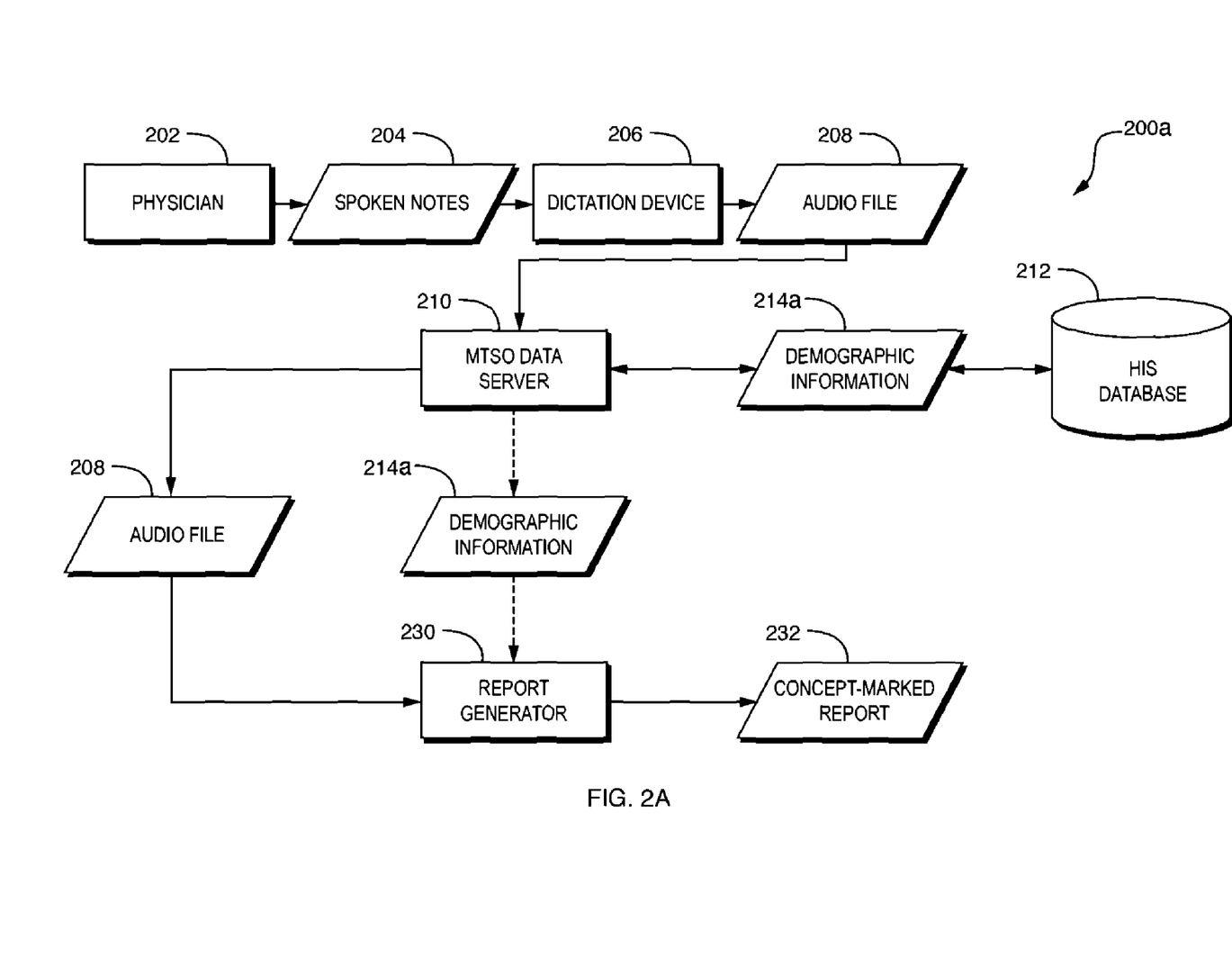
FIGS. 2A-2B are diagrams of a system for de-identifying a spoken audio signal according to one embodiment of the present invention.
Figure 2B:
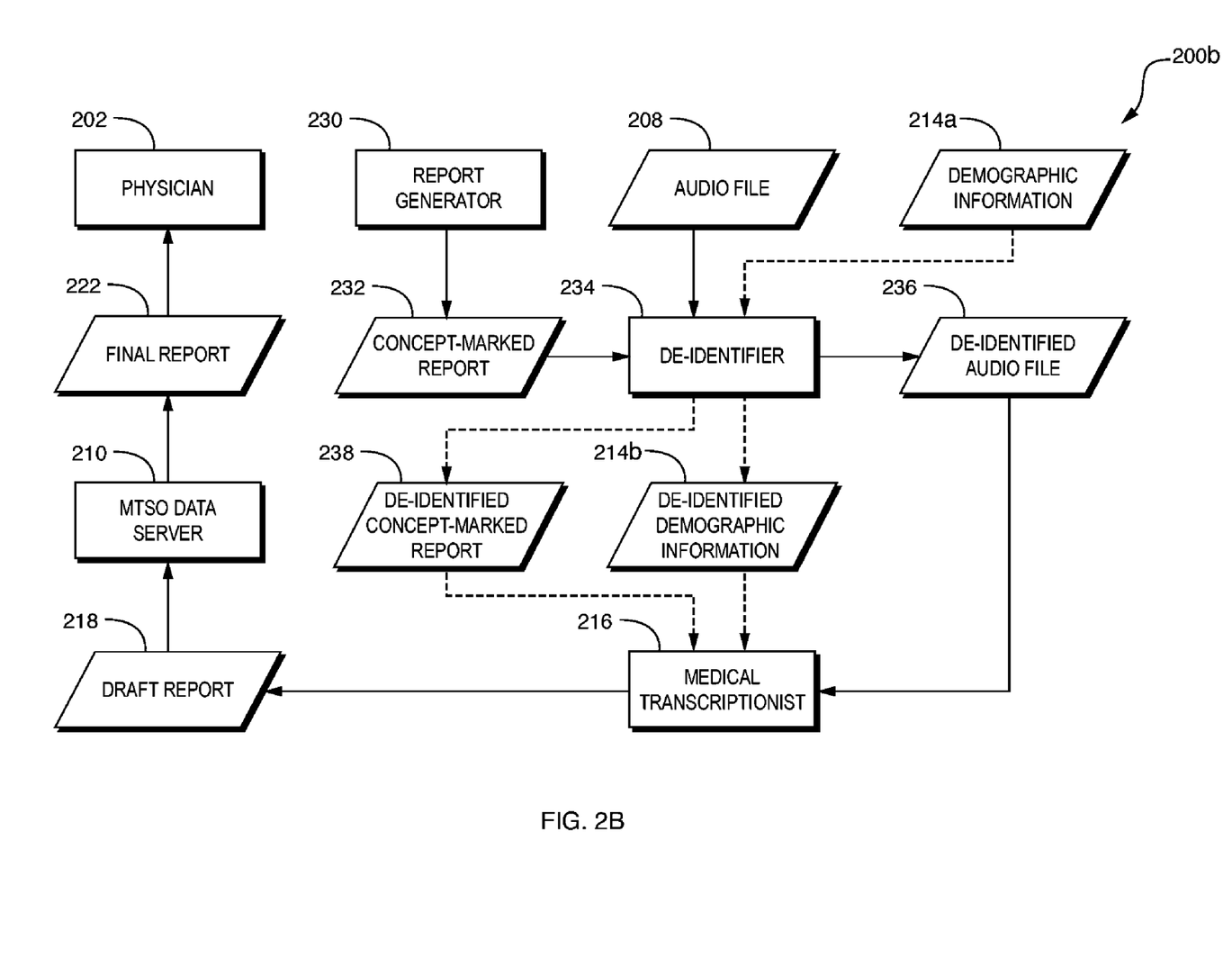
Figure 3A:
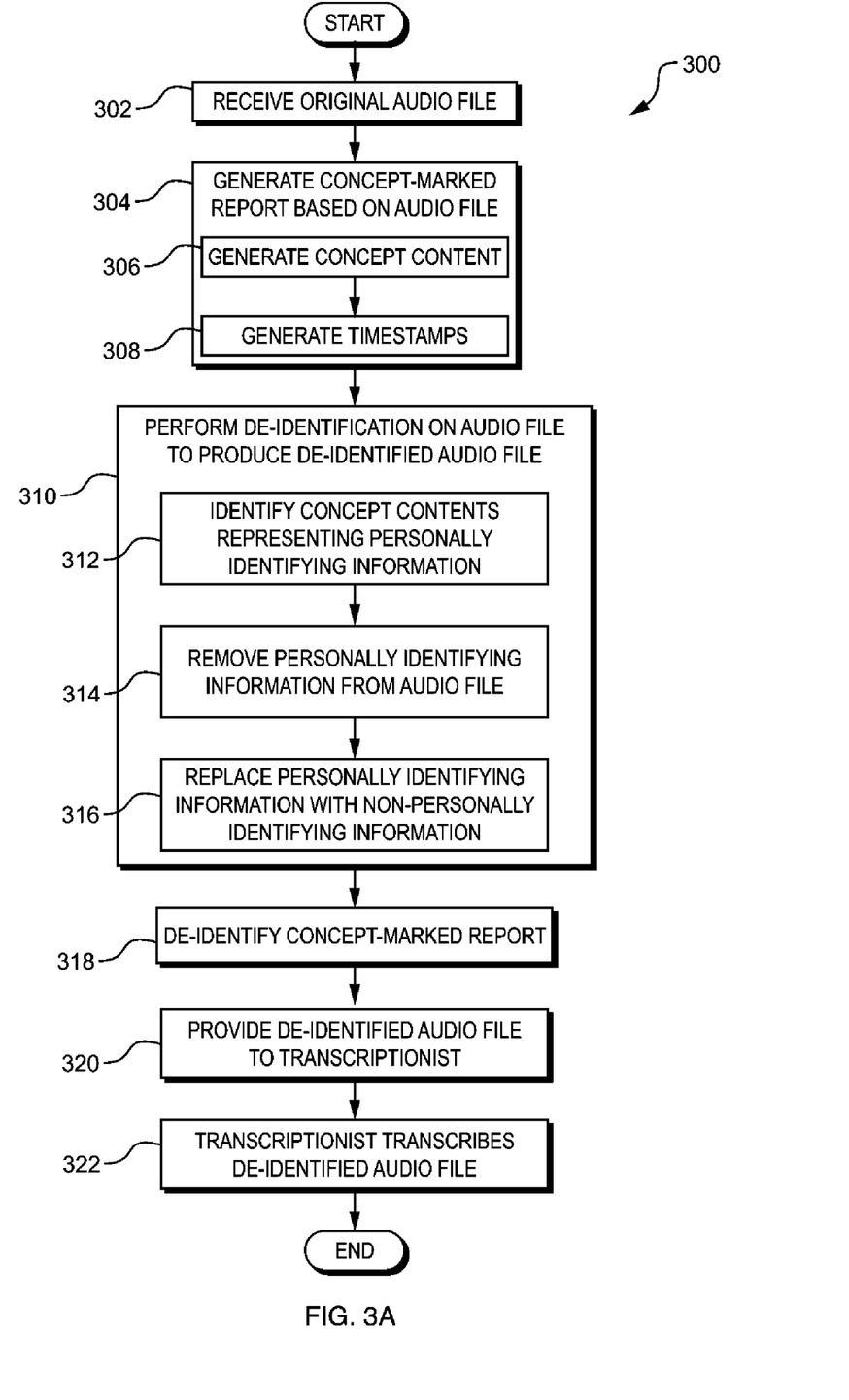
FIG. 3A is a flowchart of a method for de-identifying an audio signal according to one embodiment of the present invention.

For example, referring to FIGS. 2A-2B, a diagram is shown of the dataflow in a medical transcription system 200 using an outsourced MTSO according to one embodiment of the present invention. FIG. 2A illustrates a first portion 200a of the system 200, while FIG. 2B illustrates a second (partially overlapping) portion 200b of the system 200. Referring to FIG. 3A, a flowchart is shown of a method 300 performed by the system 200 according to one embodiment of the present invention.

In one embodiment of the present invention, a physician 202 dictates notes 204 into a dictation device 206 to produce an audio file 208, as described above with respect to FIG. 1. The audio file 208 is transmitted to a data server 210 at the MTSO. A report generator 230 receives the audio file 208 (step 302). Note that the report generator 230 may reside at the site of the MTSO. The report generator 230 generates a concept-marked report 232 based on the audio file 208 and (optionally) the demographic information 214 (step 304).

The report generator 230 may, for example, generate the concept-marked report 232 using the techniques disclosed in the above-referenced patent application entitled "Automated Extraction of Semantic Content and Generation of a Structured Document from Speech." The report 232 may, for example, include a literal or non-literal transcript of the audio file 208. Text in the report 232 that represents concepts, such as names, dates, and addresses, may be marked so that such "concept text" may be identified and processed automatically by a computer. For example, in one embodiment of the present invention, the report 232 is an Extensible Markup Language (XML) document and concept text in the report 232 is marked using XML tags. Concepts in the report 232 may be represented not only by text but also by other kinds of data. Therefore, more generally the report generator 230 generates "concept content" representing concepts that appear in the audio file 208 (step 306). The report may include not only concepts but also plain text, such as text corresponding to speech in the audio file 208 which the report generator 230 does not identify as corresponding to a concept.

The above-referenced patent application entitled "Automated Extraction of Semantic Content and Generation of a Structured Document from Speech" further describes the use of language models that are based on "concept grammars." The report generator 230 may include a speech recognizer which uses such language models to generate the concept-marked report 232. Those grammars can be configured using the demographic information that was provided with the audio recording 208. For example, a birthday grammar may be configured to expect the particular birthday of the patient that is the subject of the audio recording 208. Although such customization is not required, it may increase the accuracy of speech recognition and the subsequent report 232. If no such demographic information is available, generic slot fillers may be used. For example, name lists of the most frequent first and last names may stand in for missing patient name information.

The MTSO data server 110 may match the audio file 208 with corresponding demographic information 214a received from the HIS database 212 or another source and transmit the audio file 208 and matched demographic information 214a to the report generator 230. Such demographic information 214a may assist the report generator 230 in identifying concepts in the audio file 208. Use of the demographic information 214a by the report generator 230 is not, however, required.

The report generator 230 may also generate timestamps for each of the concept contents generated in step 306 (step 308). The timestamps indicate the temporal positions of speech in the audio file 208 that corresponds to the concept contents in the report 232.

Figure 2C:
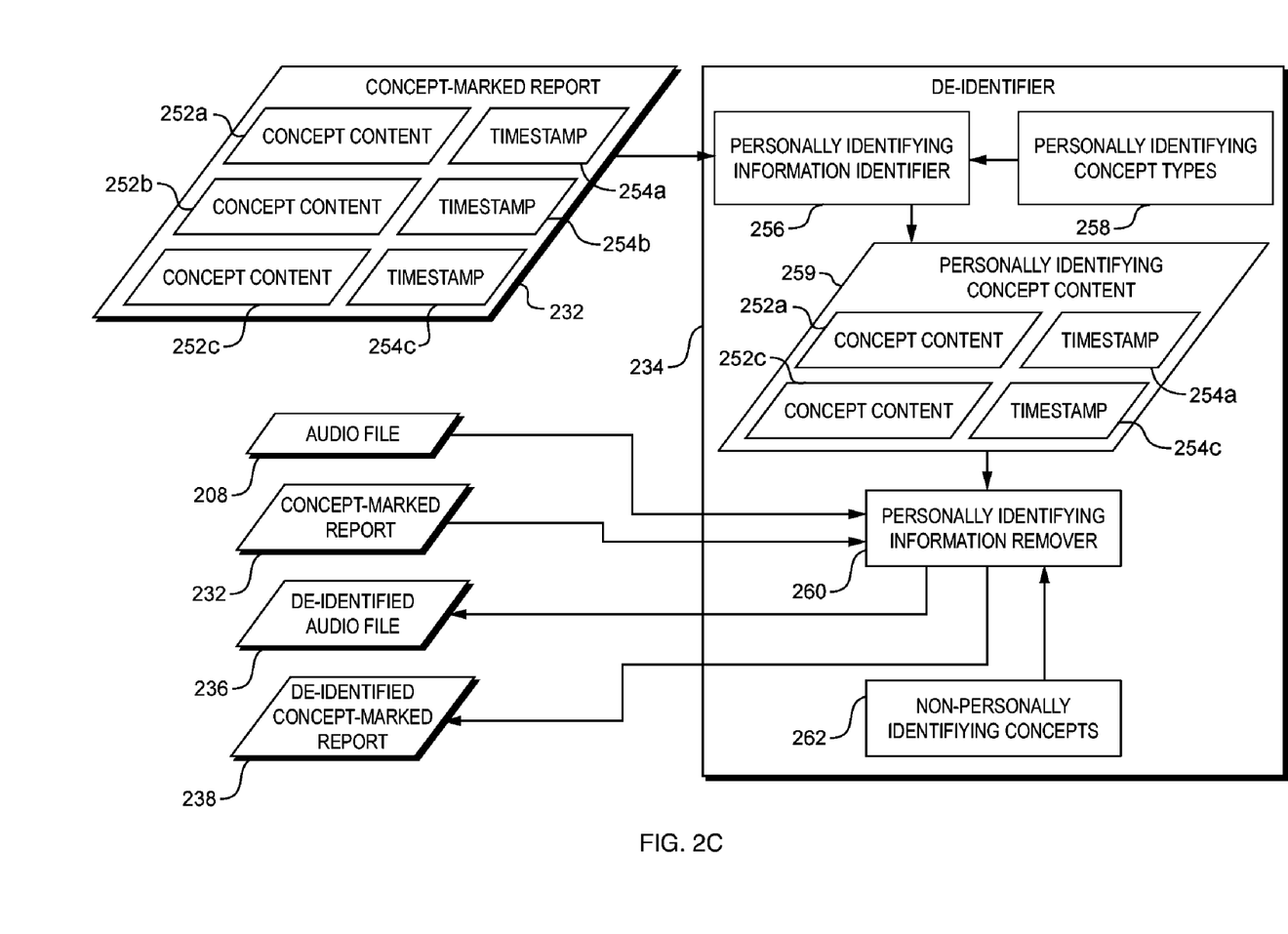
FIG. 2C is a block diagram illustrating the operation of the de-identifier of FIGS. 2B in greater detail according to one embodiment of the present invention.

Referring to FIG. 2B, the system 200 also includes an audio de-identifier 234 which receives as its input the audio file 208, the concept-marked report 232, and optionally the demographic information 214a. The de-identifier 234 removes personally-identifying information from the audio file 208 and thereby produces a de-identified audio file 236 which does not include personally identifying information (step 310). The de-identifier 234 may also remove personally identifying information from the demographic information 214a to produce de-identified demographic information 214b. The demographic information 214a may typically be de-identified easily because it is provided in a form (such as an XML document) in which personally identifying information is marked as such. Referring to FIG. 2C, a block diagram is shown which illustrates the operation of the de-identifier 234 in more detail according to one embodiment of the present invention.

In the example illustrated in FIG. 2C, the concept-marked report 232 includes three concept contents 252a-c and corresponding timestamps 254a-c. Although in practice the concept-marked report 232 may include a large number of marked concepts, only three concept contents 252a-c are illustrated in FIG. 2C for ease of illustration and explanation. Assume for purposes of example that the concept contents 252a-c correspond to sequential and adjacent portions of the audio file 208. For example, assume that the audio file 208 contains the speech "Patient Richard James, dictation of progress note, date of birth Mar. 28, 1967," that concept content 252a is the text "Richard James," that concept content 252b is the text "dictation of progress note," and that the concept content 252c is the date Mar. 28, 1967.

In the example just described, concept content 252a represents a patient name, which is an example of personally identifying information; concept content 252b represents the type of document being created, which is an example of non-personally identifying information; and concept content 252c represents the patient's birthday, which is an example of personally identifying information. Note that in this example the text "dictation of progress note" may be further subdivided into the non-concept speech "dictation of" and the non-personally identifying concept "progress note" (which is an example of a work type concept). For ease of explanation, however, the text "dictation of progress note" will simply be described herein as a non-personally identifying concept.

Figure 2D:
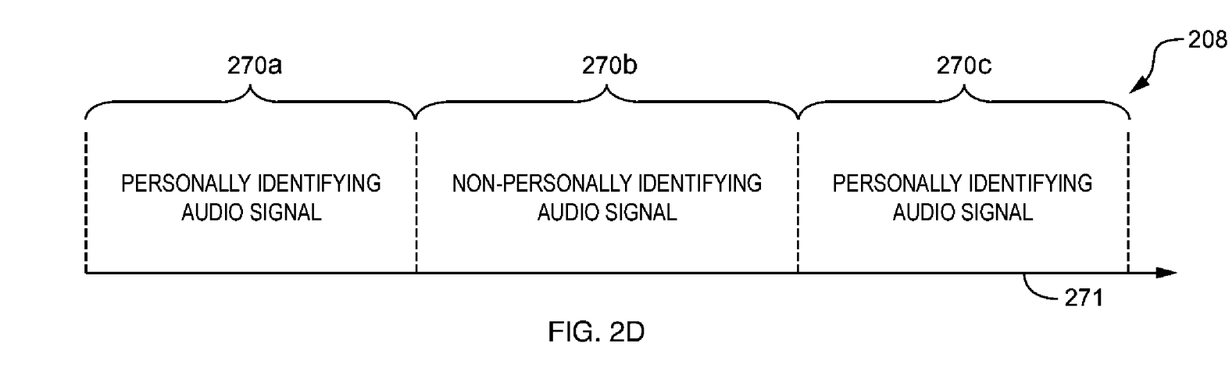
FIG. 2D is a block diagram illustrating an audio file including both personally identifying information and non-personally identifying information according to one embodiment of the present invention.

Referring to FIG. 2D, a diagram is shown illustrating the audio file 208 in the example above. Time advances in the direction of arrow 271. The audio signal 208 includes three portions 270a-c, corresponding to concept contents 252a-c, respectively. In other words, portion 270a is an audio signal (e.g., the speech "Patient Richard James") corresponding to concept content 252a (e.g., the structured text "<PATIENT>Richard James</PATIENT>"); portion 270b is an audio signal (e.g., the speech "dictation of progress note") corresponding to concept content 252b (e.g., the structured text "dictation of <WORKTYPE>PROGRESSNOTE</WORKTYPE>"); and portion 270c is an audio signal (e.g., the speech "Mar. 28, 1967") corresponding to concept content 252c (e.g., the structured text "<DATE><MONTH>3</MONTH><DAY>28</DAY><YEAR>1967</YEAR></DATE>")

Portions 270a and 270c, which correspond to a patient name and patient birthday, respectively, are labeled as "personally identifying" audio signals in FIG. 2D, while portion 270b, which corresponds to the date of an examination, is labeled as a "non-personally identifying" audio signal in FIG. 2D. Note that the particular choice of concepts which qualify as personally identifying and non-personally identifying may vary from application to application. The particular choices used in the examples herein are not required by the present invention.

Timestamps 254a-c indicate the temporal positions of speech in the audio file 208 that corresponds to concept contents 252a-c, respectively. For example, timestamp 254a indicates the start and end time of portion 270a; timestamp 254b indicates the start and end time of portion 270b; and timestamp 254c indicates the start and end time of portion 270c. Note that timestamps 254a-c may be represented in any of a variety of ways, such as by start and end times or by start times and durations.

Returning to FIG. 2C and FIG. 3A, the de-identifier 234 performs de-identification on the audio file 208 by identifying concept contents in the report 232 which represent personally identifying information (step 312). Concept contents representing personally identifying information may be identified in any of a variety of ways. For example, a set of personally identifying concept types 258 may indicate which concept types qualify as "personally identifying." For example, the personally identifying concept types 258 may indicate concept types such as patient name, patient address, and patient date of birth. Concept types 258 may be represented using the same markers (e.g., XML tags) that are used to mark concepts in the report 232. A personally identifying information identifier 256 may identify as personally identifying concept content 259 any concept contents in the report 232 having the same type as any of the personally identifying concept types 258. For example, assuming that the personally identifying concept types 258 include patient name and patient date of birth but not examination date, the personally identifying information identifier 256 identifies the concept content 252a (e.g., "<PATIENT>Richard James</PATIENT>") and the concept content 252c ("<DATE><MONTH>3</MONTH><DAY>28</DAY><YEAR>1967</YEAR></DATE>" as personally identifying concept content 259.

The de-identifier 234 may include a personally identifying information remover 260 which removes any personally identifying information from the audio file 208 (step 314). The remover 260 may perform such removal by using the timestamps 254a, 254c in the personally identifying concept content 259 to identify the corresponding portions 270a, 270c (FIG. 2D) of the audio file 208, and then removing such portions 270a, 270c.

Figure 2E:
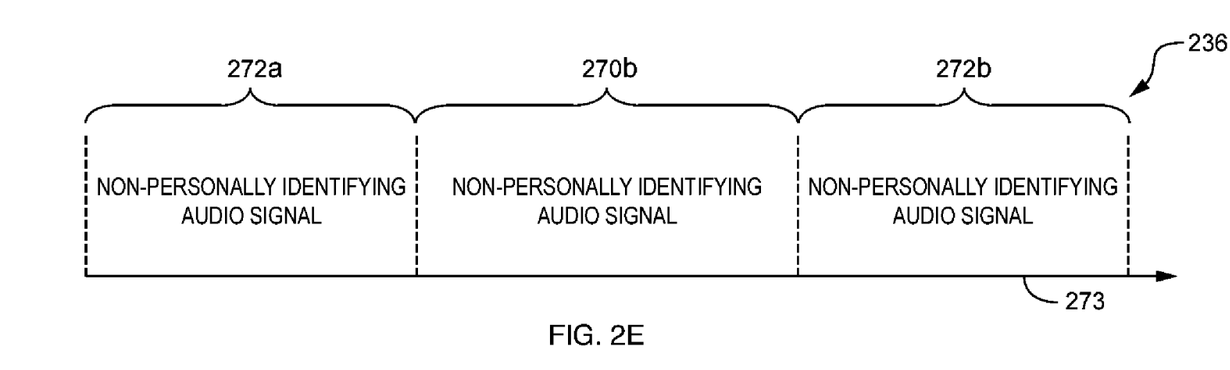
FIG. 2E is a block diagram illustrating an audio file including only non-personally identifying information according to one embodiment of the present invention.

The remover 260 may also replace the removed portions 270a, 270c with non-personally identifying information (step 316) to produce the de-identified audio file 236. A set of non-personally identifying concepts 262, for example, may specify audio signals to substitute for one or more personally identifying concept types. The remover 260 may identify substitute audio signals 272a, 272b corresponding to the personally identifying audio signals 270a, 270c and replace the personally identifying audio signals 270a, 270c with the corresponding substitute audio signals 272a, 272b. The result, as shown in FIG. 2E, is that the de-identified audio file 236 includes only non-personally identifying audio signals 272a, 270b, and 272b.

Any of a variety of substitute audio signals may be used to replace personally identifying audio signals in the audio file 208. For example, in one embodiment of the present invention, the de-identifier 234 replaces all personally identifying audio signals in the audio file 208 with a short beep, thereby indicating to the transcriptionist 216 (or other listener) that part of the audio file 208 has been suppressed.

In another embodiment of the present invention, each of the personally identifying audio portions 270a, 270c is replaced with an audio signal that indicates the type of concept that has been replaced. For example, a particular family name (e.g., "James") may be replaced with the generic audio signal "family name," thereby indicating to the listener that a family name has been suppressed in the audio file 208.

In yet another embodiment of the present invention, each of the personally identifying audio portions 270a, 270c is replaced with an audio signal that indicates both the type of concept that has been replaced and an identifier of the replaced concept which distinguishes the audio portion from other audio portions representing the same type of concept. For example, the first family name that is replaced may be replaced with the audio signal "family name 1," while the second family name that is replaced may be replaced with the audio signal "family name 2." Assuming that the audio signal "family name 1" replaced the family name "James," subsequent occurrences of the same family name ("James") may be replaced with the same replacement audio signal (e.g., "family name 1").

Although not shown in FIGS. 2A-2E, the audio file 208 may include a header portion. The header portion may include such dictated audio signals as the name of the physician and the name of the patient. In another embodiment of the present invention, the de-identifier 234 removes the header portion of the audio file 208 regardless of the contents of the remainder of the audio file 208.

The de-identifier 234 may also perform de-identification on the concept-marked report 232 to produce a de-identified concept-marked report 238 (step 318). De-identification of the concept-marked report 232 may be performed by replacing personally identifying text or other content in the report 232 with non-personally identifying text or other content. For example, the concept contents 252a and 252c in the report 232 may be replaced with non-personally identifying contents in the de-identified report 238. The non-personally identifying content that is placed in the de-identified report 238 may match the audio that is placed in the de-identified audio file 236. For example, if the spoken audio "James" is replaced with the spoken audio "family name" in the de-identified audio file 236, then the text "James" may be replaced with the text "family name" in the de-identified report 238.

The de-identifier 234 provides the de-identified audio file 236, and optionally the demographic information 214b and/or the de-identified concept-marked report 238, to a medical transcriptionist 216 (step 320). The medical transcriptionist 216 transcribes the de-identified audio file 236 to produce a draft report 218 (step 322). The transcriptionist 216 may produce the draft report 218 by transcribing the de-identified audio file 236 from scratch, or by beginning with the de-identified concept-marked report 238 and editing the report 238 in accordance with the de-identified audio file 236. The medical transcriptionist 216 may be provided with a set of pre-determined tags (e.g., "FamilyName2") to use as substitutes for beeps and other de-identification markers in the de-identified audio file 236. If the transcriptionist 216 cannot identify the type of concept that has been replaced with a de-identification marker, the transcriptionist 216 may insert a special marker into the draft report requesting further processing by a person (such as the physician 202) who has access to the original audio file 208.

One advantage of various embodiments of the present invention is that they enable the statistical de-identification of audio recordings and other audio signals. As described above, conventional de-identification techniques are limited to use for de-identifying text documents. Failure to de-identify audio recordings, however, exposes private information in the process of generating transcripts in systems such as the one shown in FIG. 1. By applying the audio de-identification techniques disclosed herein, transcription work can be outsourced without raising privacy concerns.

In particular, the techniques disclosed herein enable a division of labor to be implemented which protects privacy while maintaining a high degree of transcription accuracy. For example, the physician's health care institution typically trusts that the U.S.-based operations of the MTSO will protect patient privacy because of privacy regulations governing the MTSO in the U.S. The audio file 208, which contains personally identifying information may therefore be transmitted by the physician 202 to the MTSO data server 210 with a high degree of trust. The MTSO may then use the de-identifier to produce the de-identified audio file 236, which may be safely shipped to an untrusted offshore transcriptionist without raising privacy concerns. Because the MTSO maintains the private patient information (in the audio file 208) in the U.S., the MTSO may use such information in the U.S. to verify the accuracy of the concept-marked report 232 and the draft report 218. Transcript accuracy is therefore achieved without requiring additional effort by the physician 102 or health care institution, and without sacrificing patient privacy.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Examples of concept types representing personally identifying information include, but are not limited to, name, gender, birth date, address, phone number, diagnosis, drug prescription, and social security number. The term "personally identifying concept" refers herein to any concept of a type that represents personally identifying information.

Although particular examples disclosed herein involve transcribing medical information, this is not a requirement of the present invention. Rather, the techniques disclosed herein may be applied within fields other than medicine where de-identification of audio signals is desired.

Furthermore, the techniques disclosed herein may be applied not only to personally identifying information, but also to other kinds of sensitive information, such as classified information, that may or may not be personally identifying. The techniques disclosed herein may be used to detect such information and to remove it from an audio file to protect it from disclosure.

Although in the example described above with respect to FIGS. 2D-2E all of the personally identifying information in the audio file 208 was removed, this is not a requirement of the present invention. It may not be possible or feasible to identify and remove all personally identifying information in all cases. In such cases, the techniques disclosed herein may remove less than all of the personally identifying information in the audio file 208. As a result, the de-identified audio file 236 may include some personally identifying information. Such partial de-identification may, however, still be valuable because it may substantially increase the difficulty of correlating the remaining personally identifying information with personally identifying information in other data sources.

Figure 3B:
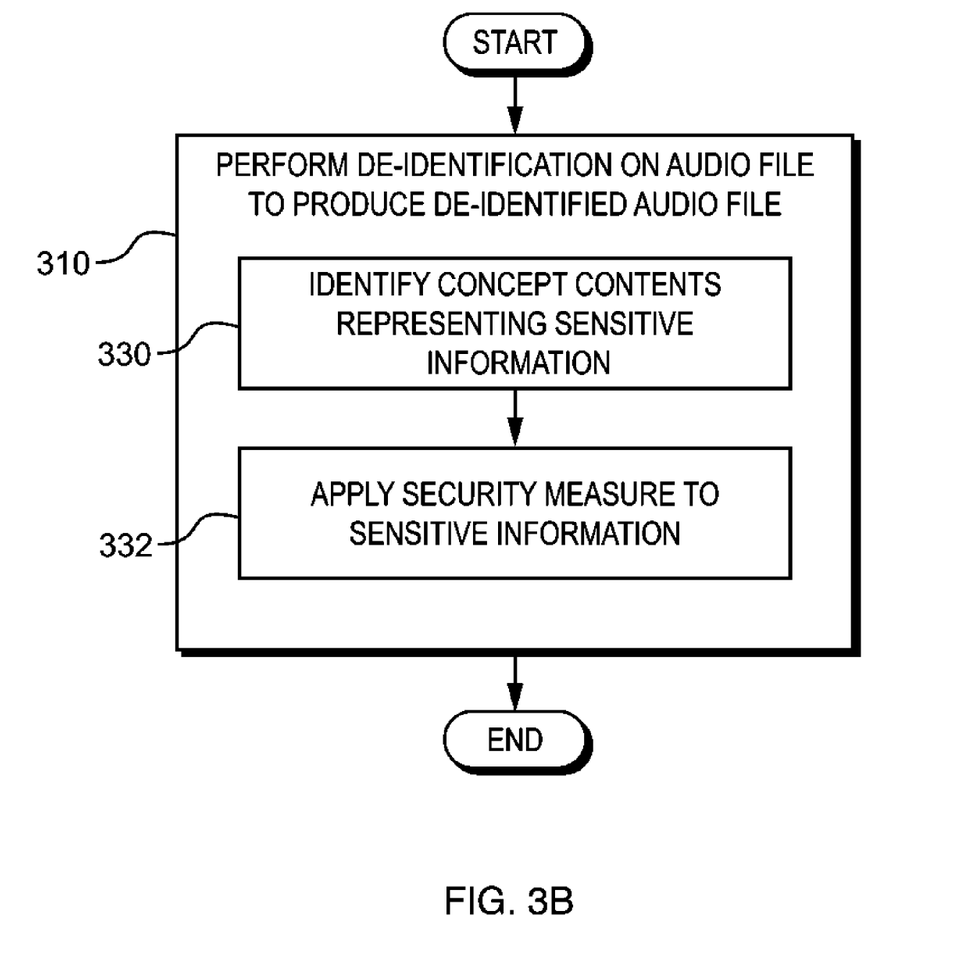
FIG. 3B is a flowchart of alternative techniques for performing a portion of the method of FIG. 3A according to one embodiment of the present invention.

Furthermore, referring to FIG. 3B, a flowchart is shown of an alternative method for implementing step 310 of FIG. 3A according to one embodiment of the present invention. The method identifies concept contents representing sensitive information (step 330) and applies a security measure to the sensitive information to protect it against unauthorized disclosure in the de-identified audio file 236 (step 332). Although the security measure may involve removing the sensitive information, as described above with respect to FIG. 3A, other security measures may be applied. For example, the sensitive information may be encrypted in, rather than removed from, the de-identified audio file 236. Sensitive information may also be protected against unauthorized disclosure by applying other forms of security to the information, such as by requiring a password to access the sensitive information. Any kind of security scheme, such as a multi-level security scheme which provides different access privileges to different users, may be applied to protect the sensitive information against unauthorized disclosure. Such schemes do not require that the sensitive information be removed from the file to protect it against unauthorized disclosure. Note that in accordance with such schemes, the entire audio file 236 (including both sensitive and non-sensitive information) may be encrypted, in which case access to the sensitive information may be selectively granted only to those users with sufficient access privileges.

Although particular examples described herein refer to protecting information about U.S. persons against disclosure to non-U.S. persons, the present invention is not limited to providing this kind of protection. Rather, any criteria may be used to determine who should be denied access to sensitive information. Examples of such criteria include not only geographic location, but also job function and security clearance status.

The techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

What is claimed is:

1. A method, performed by at least one computer processor executing computer program instructions tangibly embodied on a computer-readable medium, the method comprising:
  (A) identifying a first portion of an original audio signal, the first portion representing sensitive content, comprising:
    (A)(1) generating a report, the report comprising: (a) content representing information in the original audio signal, and (b) a timestamp indicating a temporal position of the first portion of the original audio signal;
    (A)(2) identifying a first personally identifying concept in the report;
    (A)(3) identifying a first timestamp in the report corresponding to the first personally identifying concept;
    (A)(4) identifying a portion of the original audio signal corresponding to the first personally identifying concept by using the first timestamp; and
  (B) producing a modified audio signal in which the identified first portion is protected against unauthorized disclosure by applying a security measure to the identified first portion to produce the modified audio signal, wherein the identified first portion in the modified audio signal is protected against unauthorized disclosure.

2. The method of claim 1, wherein the sensitive content comprises personally identifying content.

3. The method of claim 1, wherein (B) comprises encrypting the identified first portion.

4. The method of claim 1, wherein (B) comprises:
replacing the identified first portion with a second audio signal portion that does not include personally identifying information.

5. The method of claim 4, wherein replacing the identified first portion comprises replacing the identified first portion with a non-speech audio signal.

6. The method of claim 4, wherein replacing the identified first portion comprises replacing the identified first portion with an audio signal representing a type of concept represented by the identified first portion.

7. The method of claim 6, wherein the type of concept is one of a personal name, personal address, personal telephone number, gender, birthday, medical diagnosis, drug prescription, and social security number.

8. The method of claim 6, wherein replacing the identified first portion comprises replacing the identified first portion with an audio signal representing both a type of concept represented by the identified first portion and an identifier of the identified first portion which distinguishes the identified first portion from other portions of the original audio signal representing the same type of concept.

9. The method of claim 1, wherein (B) comprises replacing the identified first portion with a beep audio signal.

10. The method of claim 1, wherein (A) further comprises a step of identifying a header portion of the original audio signal, and wherein (B) comprises removing the identified header portion from the original audio signal.

11. The method of claim 1, further comprising:
(C) transcribing the de-identified audio signal to produce a transcript of the de-identified audio signal.

12. The method of claim 11, wherein the transcript comprises a literal transcript of the de-identified audio signal.

13. The method of claim 11, wherein the transcript comprises a non-literal transcript of the de-identified audio signal.

14. The method of claim 11, wherein (C) comprises transcribing the de-identified audio signal using an automated speech recognizer.

15. The method of claim 1, wherein the original audio signal comprises a live audio signal.

16. The method of claim 1, wherein the original audio signal comprises a recorded audio signal.

17. A computer program product comprising computer program instructions tangibly embodied on a computer-readable medium, wherein the instructions are executable by a computer processor to perform a method comprising:
(A) identifying a first portion of an original audio signal, the first portion representing sensitive content, comprising:
(A)(1) generating a report, the report comprising: (a) content representing information in the original audio signal, and (b) a timestamp indicating a temporal position of the first portion of the original audio signal;
(A)(2) identifying a first personally identifying concept in the report;
(A)(3) identifying a first timestamp in the report corresponding to the first personally identifying concept;
(A)(4) identifying a portion of the original audio signal corresponding to the first personally identifying concept by using the first timestamp; and
(B) producing a modified audio signal in which the identified first portion is protected against unauthorized disclosure by applying a security measure to the identified first portion to produce the modified audio signal, wherein the identified first portion in the modified audio signal is protected against unauthorized disclosure.

18. The computer program product of claim 17, wherein the sensitive content comprises personally identifying content.

19. The computer program product of claim 17, wherein the (B) comprises encrypting the identified first portion.

20. The computer program product of claim 17, wherein (B) comprises:
replacing the identified first portion with a second audio signal portion that does not include personally identifying information.

21. The computer program product of claim 17, wherein (A) further comprises identifying a header portion of the original audio signal, and wherein (B) comprises removing the identified header portion from the original audio signal.

22. The computer program product of claim 17, wherein the method further comprises:
(C) transcribing the de-identified audio signal to produce a transcript of the de-identified audio signal.

* * * * *

UNITED STATES PATENT AND TRADEMARK OFFICE
CERTIFICATE OF CORRECTION

| | | |
|---|---|---|
| PATENT NO. | : 8,086,458 B2 | Page 1 of 1 |
| APPLICATION NO. | : 12/258103 | |
| DATED | : December 27, 2011 | |
| INVENTOR(S) | : Michael Finke et al. | |

It is certified that error appears in the above-identified patent and that said Letters Patent is hereby corrected as shown below:

On the Title Page
In Item (45), in column 2, in "Date of Patent" line 1, before "Dec. 27, 2011" insert -- * --.

Above Item (21), under "(*) Notice", line 4, below "days." insert
-- This patent is subject to a terminal disclaimer --.

In column 6, line 27, after ")" insert -- . --.

In column 7, line 3, after "DATE>"" insert -- ) --.

Signed and Sealed this
Fourteenth Day of February, 2012

David J. Kappos
*Director of the United States Patent and Trademark Office*